United States Patent [19]
Kaufhold et al.

[11] Patent Number: 6,077,956
[45] Date of Patent: Jun. 20, 2000

[54] PROCESS FOR PREPARING 1,2,3,6-TETRAHYDRO-2,2,6,6-TETRAMETHYLPYRIDINE

[75] Inventors: Manfred Kaufhold, Marl; Udo Jegelka, Recklinghausen, both of Germany

[73] Assignee: Huels Aktiengesellschaft, Marl, Germany

[21] Appl. No.: 09/121,621

[22] Filed: Jul. 24, 1998

[30] Foreign Application Priority Data

Jul. 29, 1997 [DE] Germany .................... 197 32 589

[51] Int. Cl.$^7$ ............................... C07D 213/06
[52] U.S. Cl. ...................................... 546/252
[58] Field of Search ............................ 546/252

[56] References Cited

PUBLICATIONS

Ozhogina et al, Chem. Als vol. 113 No. 17/846, "Anomolous Stability of a diminoxylpinacone under dehydration conditions", (1990).

R. Fankhauser, et al., Helvetica Chimica Acta, vol. 49, pp. 690–695, "Synthese Von 4–Chlorpiperidinen", (With English Summary), 1966.

J. March, John Wiley and Sons, Advanced Organic Chemistry, pp. 901–903, "Reactions", 1985.

D. BORDEAUX, et al., Acta Crystallographica Section C. Crystal Structure Communications, vol. 12, No. C39, pp. 1656–1659, Synthése de radicaux libres nitroxydes Dérivés du TéTraméthyl–2,2,6,6 Tetrahydropridine–1,2,3,6; Structure de l'Epoxy–3,4 Tétraméthyl,2,6,6 Pipéridne–Oxyle, $C_9H_{16}NO_2$, With English Abstract, 1983.

A. Hassner, et al., Tetrahedron Letters, vol. 36, No. 10, pp. 1709–1712, "A Simple Method of Preparation of 7–Alkyl–7–Azabicyclo[2.2.1]Heptanes", Mar. 6, 1995.

*Primary Examiner*—John Kight
*Assistant Examiner*—Raymond Covington
*Attorney, Agent, or Firm*—Oblon, Spivak, McClelland, Maier & Neustadt, P.C.

[57] ABSTRACT

The invention relates to a process for preparing 1,2,3,6-tetrahydro-2,2,6,6-tetramethylpyridine from 4-hydroxy-2,2,6,6-tetramethylpiperidine in which 4-hydroxy-2,2,6,6-tetramethylpiperidine is dehydrated at elevated temperature in the gas phase over a solid acid catalyst.

14 Claims, No Drawings

PROCESS FOR PREPARING 1,2,3,6-TETRAHYDRO-2,2,6,6-TETRAMETHYLPYRIDINE

BACKGROUND OF THE INVENTION

1. Field of the Invention

The invention relates to a process for preparing 1,2,3,6-tetrahydro-2,2,6,6-tetramethylpyridine (hereinafter referred to as THTMP) from 4-hydroxy-2,2,6,6-tetramethylpiperidine (hereinafter referred to as TAA-ol).

2. Description of the Related Art

THTMP is of considerable interest because the industrially important 1,2,3,6-tetrahydro-2,2,6,6-tetramethylpyridin-N-oxyl can be prepared from it. Furthermore, 2,2,6,6-tetramethylpiperidin-N-oxyl, known as TEMPO, has become readily obtainable by hydrogenation and subsequent oxidation. Both N-oxyls serve as polymerization inhibitors for monomers such as acrylic acid and its esters.

Syntheses of THTMP by dehydration of TAA-ol are known from the literature. E. Fischer was able to carry out this reaction in good yield using concentrated sulfuric acid (*Chem. Ber.* 16, 1604 (1883)). However, this requires a large excess of sulfuric acid which has to be neutralized after the reaction. Reaction of TAA-ol with concentrated hydrochloric acid at elevated temperatures under pressure gives THTMP in addition to the desired chloro compound, from which THTMP is likewise obtainable by dehydrohalogenation (Frankenhauser et al., *Helv. Chim. Acta*, 49, 690 (1966)).

These and other processes described in the literature (Samtleben, *Chem. Ber.* 32, 644 (1899)) have a high consumption of chemicals, are technically complicated and are associated with problems in waste disposal.

It is therefore an object of the invention to develop a process which can be carried out without consumption of chemicals and presents no problems in waste disposal.

SUMMARY OF THE INVENTION

This object is achieved by a process for preparing 1,2,3,6-tetrahydro-2,2,6,6-tetramethylpyridine from 4-hydroxy-2,2,6,6-tetramethylpiperidine in which 4-hydroxy-2,2,6,6-tetramethylpiperidine is dehydrated at elevated temperature in the gas phase over a solid, weakly acid catalyst.

DESCRIPTION OF THE PREFERRED EMBODIMENTS

The process is advantageously carried out continuously. The reaction proceeds according to the reaction scheme

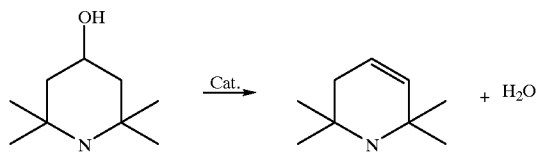

It is known that alcohols can be dehydrated in the gas phase at temperatures of from 300 to 400° C. over solid catalysts such as aluminum oxide, aluminum phosphate, thorium oxide and titanium dioxide to give the corresponding olefin. It is also known that isomerizations can be avoided in this reaction by adding an amine, e.g. piperidine. However, the amount of the amine has to be kept as low as possible because it partially poisons the acid centers of the catalyst, which can lower the activity and life of the catalyst (Organikum, Johann Ambrosius Barth, Verlag, 20th edition 262 (1996)). Surprisingly, the reaction according to the invention succeeds despite the massive concentration of NH groups in the TAA-ol starting material.

The catalyst can be present in a fixed bed, can be a moving-bed or fluidized-bed catalyst or can be stirred. Suitable catalysts are, for example, silica (or silicon dioxide), advantageously at least partly in amorphous form, and in particular acid aluminum oxides. The acid character should not be too strongly pronounced. A catalyst can be optimized, if necessary, by addition of basic substances, e.g. alkali metal or alkaline earth metal oxides or hydroxides, or of acid substances such as phosphoric acid, acid phosphates or sulfates. The amounts of basic or acid substances which bring the catalyst to its maximum performance can be readily determined by means of preliminary experiments.

In the case of aluminum oxides, the suitability as catalyst can alternatively be determined in a simple manner by suspending a known amount, e.g. 10 g, in water and adding a defined amount, e.g. 10 ml, of 0.1 M sodium hydroxide solution. The pH rises strongly at first, but over the course of from 0.6 to 2 hours it drops to a particular final value which is characteristic of the aluminum oxide used. The pH drop, i.e. the difference between the pH immediately after addition of the sodium hydroxide solution and the final value, is a measure of the acid character of the aluminum oxide. Aluminum oxides having a pH drop of from 0.5 to 2.0, preferably of from 0.6 to 1.5, are well suited as catalysts. Aluminum oxides having a lower pH drop are too weakly acidic. Aluminum oxides having a higher pH drop, for example from 2.0 to 3.5, are relatively strongly acidic, give poorer yields and are therefore, less preferred. As mentioned, catalysts which are too weakly or too strongly acidic can be optimized by addition of acid or basic substances, i.e. improved for use in the process in accordance with the invention or even made usable in practice if they were not usable before. This naturally also applies to aluminum oxides.

Silica catalysts can, if they are not directly usable as supplied, be optimized, for example, by doping them with phosphoric acid or acid phosphates.

The reaction is generally carried out at from 200 to 400° C., in particular at from 250 to 350° C., depending on the catalyst and the desired throughput. The starting material can be brought into contact with the catalyst in molten form or in solution. Suitable solvents are, for example, polar solvents such as N-methylpyrrolidone. Alcohols are also suitable as solvents. In this case, the olefin corresponding to the alcohol is obtained in addition to the desired THTMP in a codehydration. It is also possible to use the reaction product as solvent for the starting material and, thus, recirculate it to the reaction so that no solvent, which is extraneous to the reaction, has to be introduced. The melt or solution of the starting material can be fed directly to the catalyst or be vaporized beforehand in a customary vaporizer and brought into contact with the catalyst in vapor form. Particularly when a method of operation without solvent is employed, it is advisable to pass an inert gas, e.g. nitrogen or argon, co-currently together with the starting material over the catalyst.

The process can be carried out, for example, by feeding the starting material in molten (mp. 130–132° C.) or dissolved form to the heated catalyst arranged in a vertical tube reactor where it vaporizes (bp.$_{760}$ about 220° C.).

Alternatively, the starting material or its solution is introduced into a vaporizer and the vapors are passed over the heated catalyst. At the same time, an inert gas stream is passed from the top over the catalyst and this conveys the starting material and product to the lower end of the reaction zone. The conversion is monitored by determining TAA-ol in the reaction product by gas chromatography and the throughput is regulated correspondingly. A throughput of from 0.1 to 1 times, advantageously from 0.2 to 0.8 times the weight of starting material, based on the catalyst, has been found to be useful. After leaving the reactor, the reaction mixture is liquefied by cooling. Entrained condensible components in the gas stream can be separated out in a cold trap.

Having generally described this invention, a further understanding can be obtained by reference to certain specific examples which are provided herein for purpose of illustration only and are not intended to be limiting unless otherwise specified.

EXAMPLES

Example 1

A glass apparatus which comprises a vertical, electrically heatable tube having a length of 50 cm and a diameter of 3 cm, a heatable dropping funnel and a receiver with ice bath is used. The tube is charged with 150 g of aluminum oxide (SPHERALITE® SP 508 F from PROCATALYSE, Falinders, France; extruded rods having a diameter of 1.6 mm). In the test described above, the catalyst displayed a pH drop of 0.9. The dropping funnel is filled with pure TAA-ol (99.5%) and heated to 160° C. After the TAA-ol has melted, it is added drop-wise at a rate of 75 ml/h onto the catalyst heated to 280° C. At the same time, a nitrogen stream of 20 l/h is passed over the catalyst from the top. After 24 hours, the catalyst has virtually reached its full activity. 1,332 g of TAA-ol are then passed at a constant rate of 75 ml/h over the catalyst at a reaction temperature of from 300 to 315 ° C. and 1,221 g of reaction product are obtained. To work up the product, water is first removed by azeotropic distillation using cyclohexane as entrainer. Fractional distillation gives THTMP in a yield of about 70% of theoretical yield.

Example 2

The procedure of Example 1 is repeated, but using a more strongly acid aluminum oxide (SPHERALITEI® 521 E; pH drop 2.9). The yield of THTMP is only 15% of the theoretical yield. Mainly low-boiling dissociation products are formed.

Examples 3 to 5

The procedure of Example 1 is repeated using the more strongly acid aluminum oxide (SPHERALITEO® 521 E from Example 2) which has, however, previously been impregnated with sodium hydroxide, strontium hydroxide or barium hydroxide solution and dried, so that the content of the respective hydroxide, calculated as oxide, is 1% by weight.

These three catalysts gave the following yields:
Example 3, SP 521 E with 1% of $Na_2O$: about 25% of the theoretical value
Example 4, SP 521 E with 1% of SrO: about 60% of the theoretical value
Example 5, SP 521 E with 1% of BaO: about 58% of the theoretical value

Example 6

The reactor used is a quartz tube having a diameter of 35 mm and a length of 80 cm which is heated by means of an electric oven. The reactor is charged in the middle with 202 g of the acid aluminum oxide, SPHERALITE® 508 F used in Example 1, which has, however, been doped, as described in Examples 3 to 5, with 0.5% by weight of BaO. Quartz chips are located above and below the catalyst. A temperature of 330° C. is set in the reactor. Crude TAA-ol (95%) is passed through a vaporizer operated at 260° C. and introduced in vapor form into the reactor at the top. The throughput is 180 ml of crude TAA-ol per hour and 1.5 1/h of nitrogen are simultaneously passed through the vaporizer and the reactor. The yield of THTMP increases greatly during the first few hours and after about 100 hours settles down to about 82% of the theoretical value. Even after a week, the catalyst still has the same activity.

Comparative Example 1

The procedure of Example 1 is repeated but using a neutral aluminum oxide (SPHERALITE® SP 512; pH drop <0.1). No THTMP is formed at the reaction temperature of from 300 to 315° C. When the temperature is increased by 50° C., a yield of THTMP of <1% of the theoretical value is obtained at a TAA-ol conversion of 33%.

Example 7

The procedure of Example 1 is repeated, but using a catalyst which comprises partly amorphous and partly crystalline silica which is impregnated with phosphoric acid. The phosphoric acid content is 35% by weight. The yield of THTMP achieved using this catalyst is 45% of the theoretical value.

Comparative Example 2

The procedure of Example 7 is repeated, but using neutral, amorphous silica, namely silica gel KC Siliperl® AF 125 from Engelhard Industries, as catalyst. The yield of THTMP is <2% of the theoretical value.

What is claimed is:
1. A process for preparing 1,2,3,6-tetrahydro-2,2,6,6-tetramethyl-pyridine from 4-hydroxyl-2,2,6,6-tetramethylpiperidine, which comprises dehydrating 4-hydroxy-2,2,6,6-tetramethylpiperidine in the gas phase over a solid acid catalyst.

2. The process of claim 1, wherein the reaction is carried out continuously.

3. The process of claim 1, wherein the solid acid catalyst is selected from the group consisting of aluminum oxide, aluminum phosphate thorium oxide titanium dioxide and silica.

4. The process of claim 1, wherein the solid acid catalyst used is an aluminum oxide having a pH drop of from 0.5 to 2.0.

5. The process of claim 1, wherein the solid acid catalyst used is an aluminum oxide having a pH drop of from 0.6 to 1.5.

6. The process of claim 1, wherein said solid acid catalyst is in the presence of a basic substance or an acid substance.

7. The process of claim 6, wherein said basic substance is selected from the group consisting of alkali metal, alkaline earth metal oxide and alkaline earth metal hydroxide, and wherein said acid substance is selected from the group consisting of phosphoric acid, acid phosphate and acid sulfate.

8. The process of claim 1, wherein the solid acid catalyst used is silica which has been doped with phosphoric acid or an acid phosphate.

9. The process of claim 1, wherein the dehydrating is carried out at temperature range from 200 to 400° C.

10. The process of claim 1, wherein the dehydrating is carried out at temperature range from 250 to 350° C.

11. The process of claim 1, wherein TAA-ol is used in solution in a solvent selected from the group consisting of a polar solvent and the reaction product.

12. The process of claim 11, wherein said solvent is a polar solvent.

13. The process of claim 11, wherein said solvent is the reaction product.

14. The process of claim 1, wherein the reaction is carried out in the presence of an inert gas.

* * * * *